United States Patent [19]
Daoud et al.

[11] Patent Number: 5,336,174
[45] Date of Patent: Aug. 9, 1994

[54] FLOW CONTROL VALVE

[75] Inventors: Adib G. Daoud, San Diego; Emmett B. Anderson, Santee, both of Calif.

[73] Assignee: Ivac Corporation, San Diego, Calif.

[21] Appl. No.: 881,745

[22] Filed: May 7, 1992

[51] Int. Cl.$^5$ .......................................... A61M 39/00
[52] U.S. Cl. ........................................ 604/30; 604/31; 604/33; 604/65; 604/246; 604/249; 128/912
[58] Field of Search .................... 128/912; 251/149.8, 251/342, 343, 344, 346–347, 349, 354; 604/30–31, 33, 65, 246–247, 249; 251/342, 343, 344, 346–347, 354

[56] References Cited

U.S. PATENT DOCUMENTS

| | | |
|---|---|---|
| 2,088,656 | 8/1937 | Lamb . |
| 2,995,144 | 8/1961 | Manning et al. . |
| 3,570,484 | 3/1971 | Steer . |
| 3,806,086 | 4/1974 | Cloyed . |
| 3,971,541 | 7/1976 | Griffin . |
| 4,265,428 | 5/1981 | Rosemeier et al. . |
| 4,430,073 | 2/1984 | Bemis et al. ............. 604/65 |
| 4,689,043 | 8/1987 | Bisha . |
| 4,856,756 | 8/1989 | Combs ................... 251/343 |
| 4,904,236 | 2/1990 | Redmond et al. . |
| 5,116,021 | 5/1992 | Faust et al. . |
| 5,148,830 | 9/1992 | Liu ....................... 251/344 |

FOREIGN PATENT DOCUMENTS

| | | |
|---|---|---|
| 0028601 | 1/1980 | European Pat. Off. . |
| 2936496 | 9/1978 | Fed. Rep. of Germany . |
| 3003398 | 2/1979 | Fed. Rep. of Germany . |
| 3202422 | 7/1983 | Fed. Rep. of Germany . |

*Primary Examiner*—Randall L. Green
*Assistant Examiner*—P. Zuttarelli
*Attorney, Agent, or Firm*—Fulwider, Patton, Lee & Utecht

[57] ABSTRACT

A valve for fluids employs two telescoping parts which cooperate with one another to block fluid flow when pulled partially apart and open a flow path therethrough when pushed together. A plunger component, having a central bore, a closed off end and perforated walls, is slidingly and sealingly received within the collar of the hollow valve body. When the plunger's closed end is pushed far enough into the valve body so as to expose the apertures, fluid is free to flow from within the valve body into the plunger component. When pulled apart so as to cause the perforations to be positioned within the confines of the collar, flow is blocked. An actuation mechanism integrated into a housing serves to automatically pull the valve's components apart to stop flow when its cover is swung open and conversely causes the two components to be pushed together to open flow when the cover is closed.

26 Claims, 4 Drawing Sheets

FLOW CONTROL VALVE

BACKGROUND

The present invention relates generally to valves and more particularly, to valve configurations that are suitable for intravenous (IV) administration set applications while readily lending themselves to mechanized activation.

The control of fluid flow through an IV administration line from a fluid source to a patient is of primary concern in infusion systems. In many cases, infusion devices such as pumps or controllers are used with the IV administration set in the infusion of medical solutions to patients. These devices typically include a means which continually occludes the IV tubing to prevent free flow, although the position of occlusion may move during operation. For example, in the case where a peristaltic mechanism of some type is used, the mechanism creates a moving zone of occlusion to move the fluid at a controlled rate from the fluid source to the patient. The tubing is always occluded at one position or another. Other types of infusion devices may use valves to sequentially occlude the tubing. Thus, while the tubing of the administration set is engaged with the infusion device, most, if not all, infusion devices occlude the tubing thereby preventing free flow of the supply fluid to the patient. However, before and after the tubing is engaged with the infusion device, free flow of the IV fluid is possible and is a concern.

A large variety of valve mechanisms and valve configurations have been devised to fulfill a variety of different requirements. The requirements specific to IV set applications include low cost, as such devices are typically intended to be disposable, and ease of manipulation, preferably such that the valve can readily be actuated by a simple automated mechanism as well as manually. Many devices utilized in IV set-type applications have either been of simple, consequently inexpensive design and rather awkward to manipulate or alternatively, relatively easy to actuate but inordinately complex and therefore expensive.

An example of the former is a pinch clamp that is fastened about the exterior of resilient tubing. Opposing surfaces are brought to bear against the tubing's exterior to pinch its walls shut to prevent flow while two adjoining, appropriately configured surfaces cooperate to function as a ratchet mechanism in order to maintain the clamp in a closed or partially closed position. Squeezing the two opposing surfaces together shuts off flow while separating the two adjoining surfaces permits flow. Although such a device is of one-piece construction, two very different movements are required to open and to close the valve thereby rendering the valve rather difficult to adapt to a simple automated actuation mechanism.

An example of a device that requires a relatively simple movement to actuate is that disclosed in U.S. Pat. No. 3,971,541 to Griffin. A pulling action on a pull ring causes the valve to open while release thereof allows the valve to automatically return to its closed position. However, the valve employs numerous parts including a plunger, sealing plug, two biasing means, O-rings, etc. thereby resulting in a rather expensive unit.

The valve provided by Cloyd, U.S. Pat. No. 3,806,086 relies on fewer parts than does the Griffin valve but actuation calls for somewhat more complex movement, requiring the insertion of a supply line thereinto in order to depress a stem element which serves to open a flow path. Removal of the supply line allows a spring to urge the stem back into its closed position thereby preventing flow. While this mechanism is very simple to actuate manually, it appears rather ill-suited for mechanical manipulation. In addition, no less than four parts are incorporated in the design.

In the prior art, manually actuated flow stop clamps have been used to prevent free flow during periods when the administration set is not engaged with the infusion device. However, operation of the manually actuated clamp requires further responsibility on the part of the operator to assure that the clamp is in the correct position. For example, before engagement with the infusion device, the operator must assure that the clamp is closed to prevent flow. After engagement with the infusion device, the operator must assure that the clamp is open to permit flow so that the infusion device can move the fluid to the patient. And, before removal of the tubing from the infusion device, the operator must once again assure that the clamp is closed to prevent flow. A system which automatically performs the above operations would be preferable.

Additionally, a flow control device which indicates its current operational status to the operator is desirable. For example, a positive click indicating that the valve has been placed in the open or "flow" position and a positive click indicating the valve has been place in the closed or "flow stop" position are desirable. Some degree of confidence is then instilled in the operator that the flow control device is actually in the desired configuration.

Hence, those concerned with infusion systems have recognized that it would be of value to provide an automated system which would prevent free flow through an IV administration set connected between a fluid supply and a patient during times when the administration set is not engaged with an infusion device, which will permit flow when the administration set is engaged with the infusion device and which will simplify the infusion procedure. Additionally, it has been recognized that it would be of value to provide a flow control valve which is relatively easy and inexpensive to manufacture and which clearly indicates to the user its operational configuration. The present invention fulfills these needs.

SUMMARY OF THE INVENTION

Briefly and in general terms, the flow control valve according to the present invention comprises a hollow valve body and a perforated plunger component. The valve body connects at one end to a first conduit and has an opening at its other end in the form of an elongated collar of reduced diameter. The plunger component has a central bore, connects at one end to a second conduit and is closed off at its other end. The plunger is perforated and has a plurality of apertures formed in the plunger component's walls between the open and closed-off ends. The plunger is dimensioned such that its closed end is inserted into the valve body's interior through the collar. Annular ridges formed on the plunger's surface serve to sealingly engage the collar's inside surfaces. Annular ridges on the collar also aid in sealing surfaces and cooperate with the ridges on the plunger component to aid in positioning the two in relation to each other and positively indicate to the operator that position.

The flow control valve in accordance with the invention is opened to permit flow by telescoping its two parts into one another and closed to prevent flow by telescoping its two parts partially out of one another. By pushing the plunger component far enough into the valve body such that its perforations clear the reduced diameter of the collar, fluid in the valve body received from the first conduit is free to flow through the apertures into the plunger's central bore and out into the second conduit. Conversely, pulling the two components partially apart so as to position the plunger's apertures entirely within the collar prevents the entry of fluid into those apertures and shuts off flow.

The plunger component's ridges engage the collar's interior surface prevent the escape of fluid to the valve's exterior as well as prevent the seepage of fluid into the plunger's central bore while the valve is in its closed position. Additionally, as mentioned above, the ridges formed on the plunger component aid in sealing, positioning and indicating the relative position of the two components.

Shoulders molded into the exterior surfaces of the two components allow the two components to be easily grasped by an actuating mechanism, and by virtue of the one dimensional or telescoping interaction of the two components, only a simple reciprocating movement of such actuating mechanism is required to actuate the valve. The actuating mechanism may optionally be spring loaded such that movement in one direction is automatic. The design of the flow control valve readily lends itself to mechanical manipulation as, for example, by a device integrated into a housing and cooperating with the movement of a door or cover such that flow is automatically stopped when the door is opened and permits manual actuation for priming and for other reasons.

Other aspects and advantages of the invention will become apparent from the following detailed description and accompanying drawings, illustrating by way of example the features of the invention.

DETAILED DESCRIPTION OF THE PREFERRED EMBODIMENT

Figure 1:
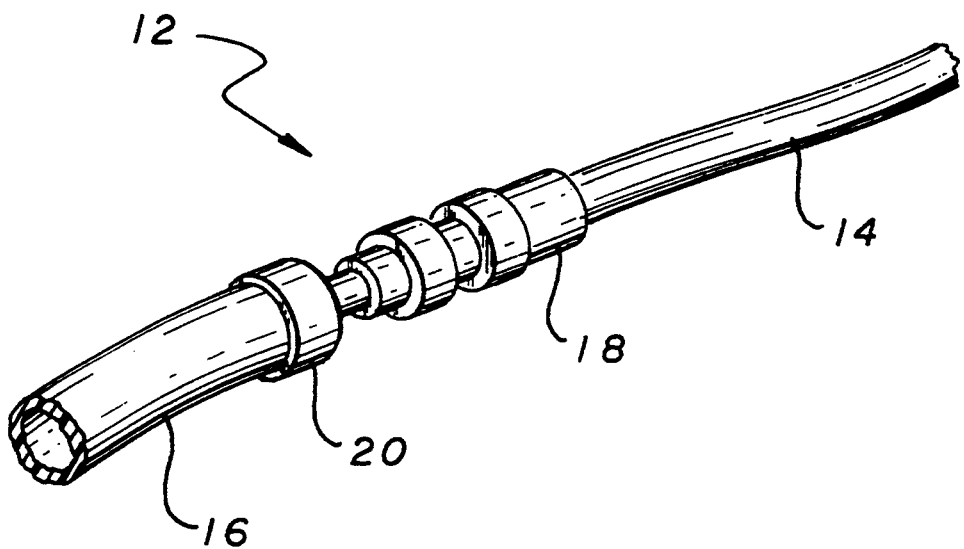
FIG. 1 is a perspective view of a flow control valve in accordance with the present invention, connected between first and second conduits.

Referring now to the drawings with more particularity, wherein like reference numerals designate like or corresponding elements among the several views, there is shown in FIG. 1 a fluid control valve 12 according to the present invention. The valve 12 is installed in-line between a first conduit 14 and a second conduit 16 to control the flow of fluid through the conduits. The valve is especially well suited for an IV administration set application.

Figure 2:
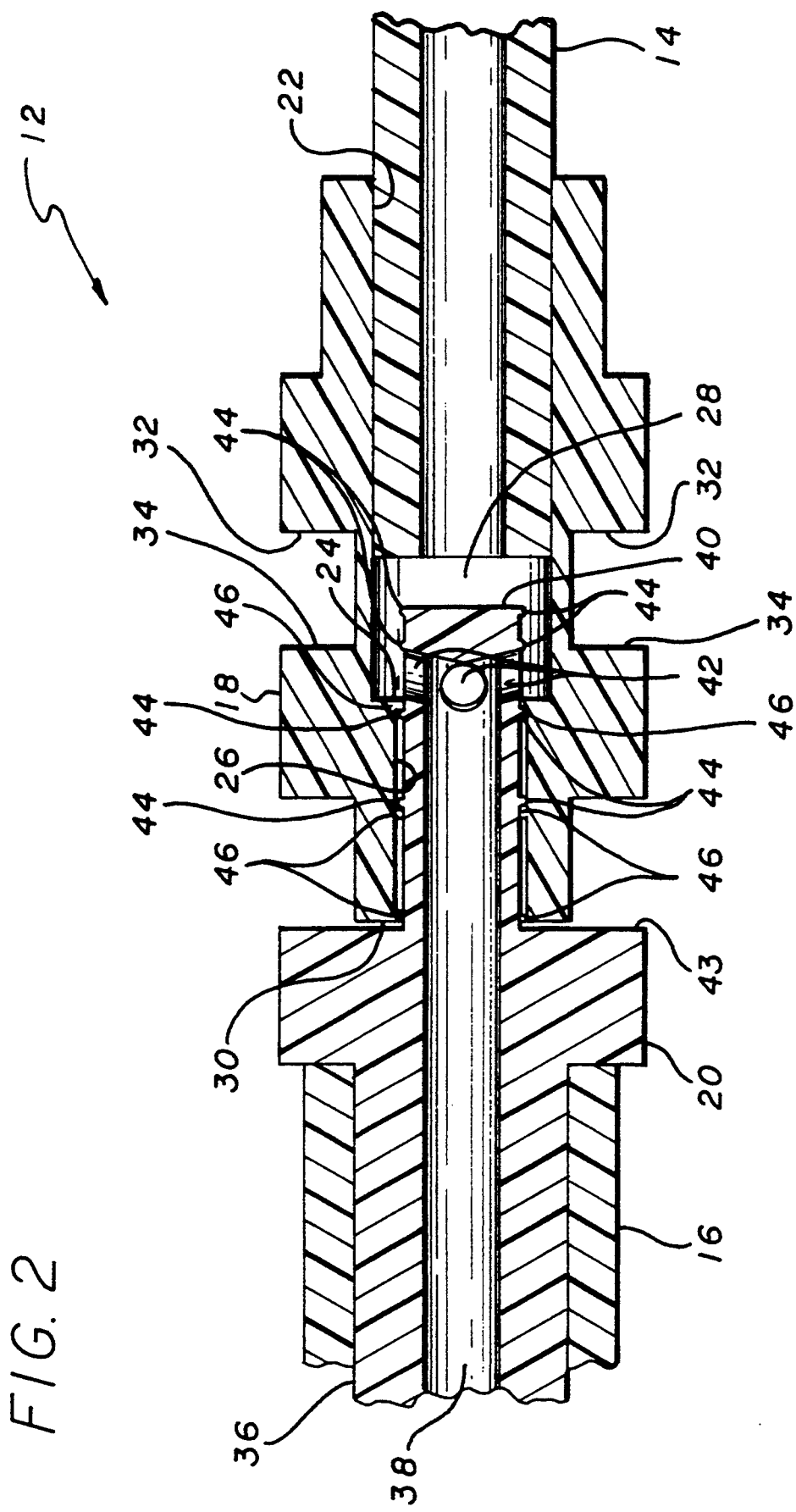
FIG. 2 is an enlarged cross-sectional view of the interior of the valve body and plunger component.

Referring now to FIG. 2, valve 12 comprises two components, a hollow valve body 18 and a perforated plunger component 20. A first port 22 includes a Luer-type connector formed at one end of the body 18 so as to enable interconnection with the first conduit 14. In the embodiment illustrated, this interconnection is achieved by an interference fit between the conduit's exterior surface and the interior wall of the connector.

The interior walls of the valve body 18 are cylindrical and include an elongated collar 24 having walls 26 of reduced diameter. A cavity 28 is thus formed which is in fluid communication with the first port 22. A second port 30 is formed at the other end of the valve body 18. In the embodiment illustrated, the exterior of the valve body 18 is generally cylindrical and additionally incorporates two annular shoulders 32 and 34 of rectangular cross-section.

The plunger component 20 of the valve 12 includes a port 36 formed at one end so as to facilitate interconnection to the second conduit 16. In the embodiment illustrated, the conduit 16 is fitted about the exterior of the plunger component's end.

The plunger component 20 has a hollow interior comprising a longitudinal bore 38 formed in its interior which is in fluid communication with the second conduit 16 connected at its port 36. The opposite end of the plunger component 20 is closed off 40 and the walls near the closed-off end 40 are perforated with a plurality of apertures 42. Part of the exterior of the plunger component 20 is dimensioned to be slidingly received within the valve body's collar 24 and is of sufficient length so that the apertures 42 in the wall of the plunger component 20 clear the reduced diameter collar 24 and extend into the cavity 28. Thus, when telescoped into the cavity 28, fluid can flow into the apertures 42 from the cavity 28, through the hollow interior of the plunger component and through the second conduit 16. The plunger component also includes a shoulder 43 to limit its movement into the valve body 18.

A series of annular ridges 44 are formed on the plunger components' 20 exterior wall to provide for a sealing engagement with the collar's 24 interior surface 26. An interference fit is established between the annular ridges 44 and the interior surface 26 of the collar 24. The ridges may be formed of a pliable material such as Hytrel ®. In this embodiment, two ridges 44 are positioned above the apertures 42 and two below.

Additionally, in the embodiment shown in FIG. 2, three annular ridges or protrusions 46 are formed on the surface 26 of the collar 24. These ridges 46 also provide a seal between the plunger component 20 and the collar 24 but are primarily used to indicate to the user the relative positions of the body 18 and plunger component 20. The ridge 44 nearest the cavity 28 cooperates with the two ridges 44 of the plunger component adjacent the closed end. When the plunger component 20 is partially telescoped out of the body 18, the top ridge 46 of the collar will be located between the two top ridges 44 of the plunger. An increased force will be felt as the plunger is telescoped out of the body and an audible click will be heard as the ridges are pulled over one another. The other two ridges of the plunger component 20 will similarly interact with the other ridges of the collar to aid in indicating the position of the components relative to each other. Similarly, as the plunger component is telescoped into the cavity 28, clicks will be heard. The ridges are also numerous enough and rigid enough to prevent inadvertent and undesirable relative movement of the body 18 and plunger 20 once positioned.

Figure 3:
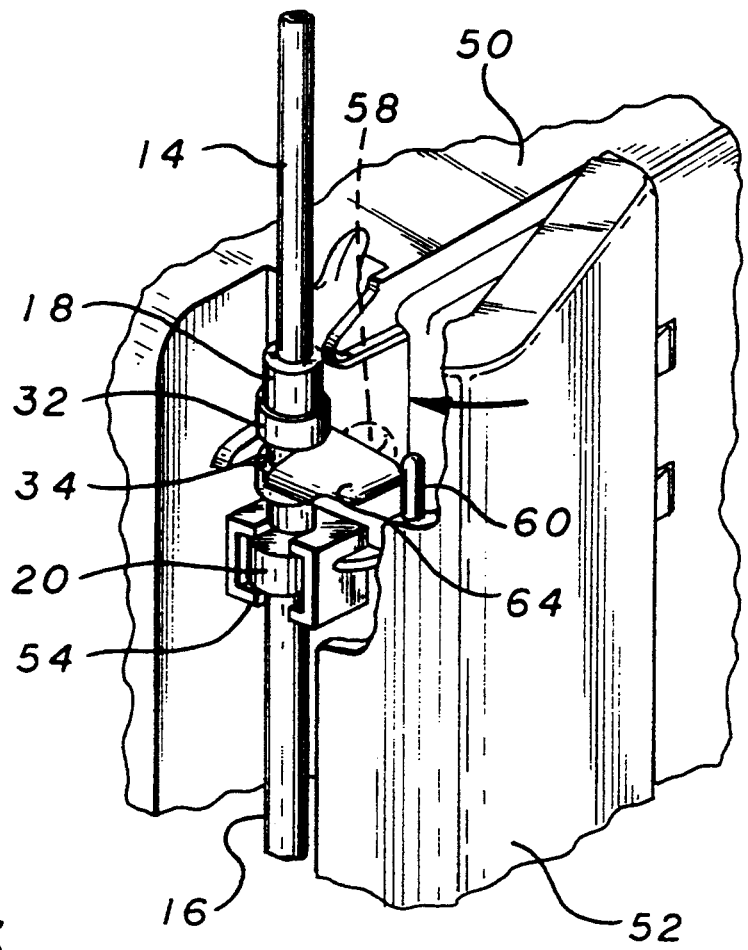
FIG. 3 is a perspective view illustrating the valve as accommodated in an automated actuation mechanism installed in an infusion device.

FIG. 3 illustrates the valve 12 in cooperation with an actuation mechanism which has been integrated into an infusion pump housing 50 such that the valve 12 is actuated upon movement of the door 52. The plunger component 20 is firmly held in place about its external shoulder 43 by a stationary clamp 54 mounted to the housing 50 while a second clamp in the form of a movable actuation arm 56 engages the valve body between its two annular shoulders 32 and 34. The actuation arm 56 is hingedly attached to the pump housing 50 and is biased upwardly by a spring 58. A pin 60 is rigidly attached to and extends from the housing door 52 and is configured and positioned to engage the arm's actuation plate 62 and urge it downwardly as the door 52 is swung closed about its hinged axis. The leading edge 64 of the actuation plate 62 is slightly downturned to facilitate proper engagement with the pin 60.

In the configuration illustrated in FIG. 3, the upwardly biased actuation arm 56 maintains the two valve components 18 and 20 in a partially pulled apart relationship until the door 52 is closed. Closing the door 52 causes the pin 60 to press the actuating arm 56 downward overcoming the bias generated by the spring 58, causing the valve body 18 to be moved towards the plunger component 20. This is shown in greater detail in FIGS. 4 and 5.

Figure 4:
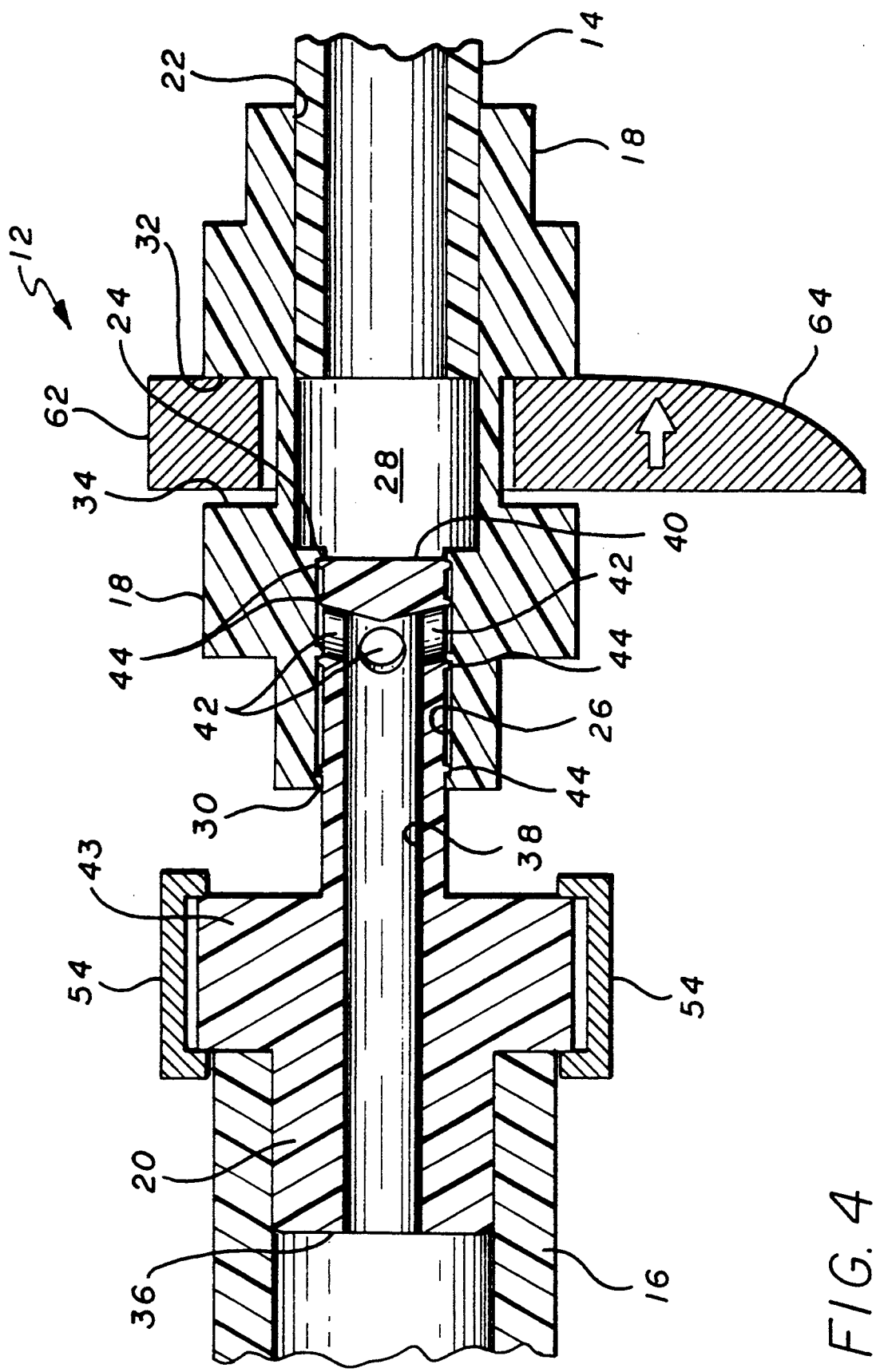
FIG. 4 is a cross-sectional view of the valve of FIG. 1 showing the valve urged into its closed position by an actuation mechanism.
Figure 5:
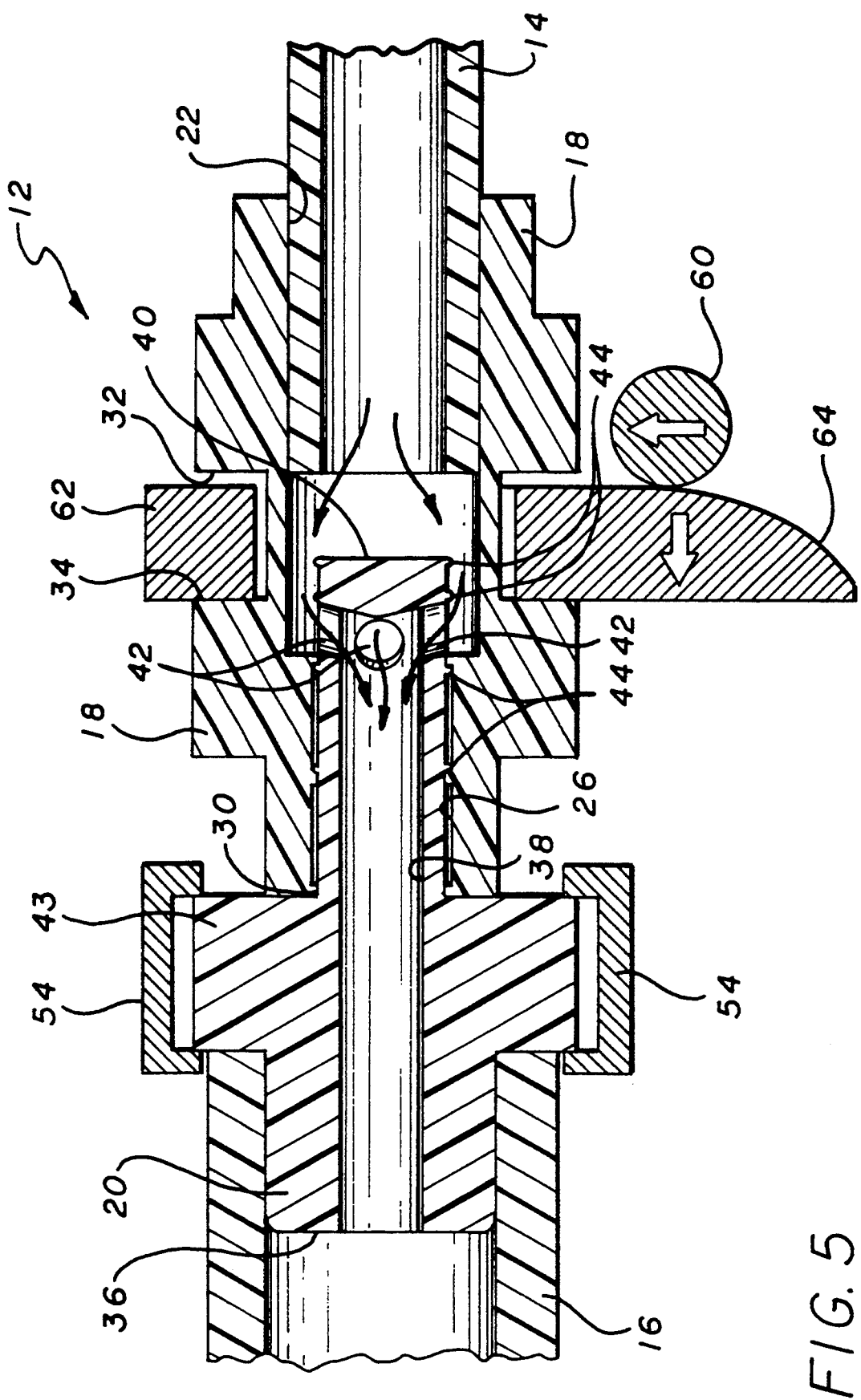
FIG. 5 is a cross-sectional view of the valve and actuation mechanism of FIG. 2 in which the valve has been urged into its open position by the actuation mechanism.

Referring now to FIGS. 4 and 5, the conduits 14 and 16 are simply slipped onto or into the valve's 12 respective ends. By maintaining the two parts in the slightly pulled apart position illustrated in FIG. 4, the flow of fluid supplied by conduit 14 is blocked as the retracted closed end 40 of the plunger component 20 creates a dead end within the collar 24 of the valve body 18. The engagement of the collar's interior wall by the annular ridges 44 ensures that no fluid escapes from the cavity 28 of the valve body into the plunger component 20.

By pushing the plunger component 20 further into the valve body 18 so as to position the apertures 42 within the valve body's interior 42 as shown in FIG. 5, a flow path is provided for fluid between the first conduit 14 and the second conduit 16. Fluid is free to flow from the first conduit 14, into the cavity 28, around the plunger component's closed end 40, through the apertures 42, into the plunger component's interior bore 38 and on through the second conduit 16. The annular ridges 44 sealingly engage the collar's 24 interior wall 38 to preclude any leakage of fluid therefrom.

The operation of the actuation mechanism shown in FIG. 3 is also shown in FIGS. 4 and 5. In FIG. 4, the pin 60 of the door is not in engagement with the actuation plate 62, thus the bias spring 58 (FIG. 3) causes the hinged arm 62 to pull the body 18 away from the plunger component 20 into the flow stop position. As mentioned above, the rigidity and number of the ridges, both on the plunger component and on the collar, prevent the plunger component from being fully pulled out of the valve body. Also, the travel distance of the actuating plate 62 is limited.

In FIG. 5, the pin 60 has engaged the actuating plate 62 and forced it downward overcoming the biasing force of the spring 58 (FIG. 3). This action has telescoped the body 18 and plunger component 20 together until the stop surface 43 of the plunger component encounters the second port 30 of the body 18. In this position, the apertures 42 are positioned in the cavity of the valve body and fluid is permitted to flow through the valve 12.

The valve's two components 18 and 20 are preferably injection molded wherein the valve body is preferably formed of PVC or ABS while the plunger component is formed of Hytrel. The inherent resiliency of Hytrel allows the annular ridges 36 to form a tight seal against the collar 24.

While a particular form of the invention has been illustrated and described, it will also be apparent to those skilled in the art that various modifications can be made without departing from the spirit and the scope of the invention. Accordingly it is not intended that the invention be limited except by the appended claims.

What is claimed is:

1. An apparatus for controlling fluid communication between a first and a second conduit, comprising:

a valve body having a first port, a second port, and an interior cavity, said cavity having a first portion having a diameter and a second portion having a diameter and a first and a second end, said diameter of said second portion being substantially the same between said first end and said second end, wherein both said first and second ports are in fluid communication with said interior cavity and said first port is connected to the first conduit, wherein said diameter of said first portion of the interior cavity is larger than said diameter of said second portion, and said first portion is closer to said first port than said second portion is to said first port;

a plunger component having a closed end, a hollow interior and a third port connected to the second conduit and to said hollow interior, said plunger component having a side wall connecting said third port with said closed end, said side wall having an aperture positioned therein adapted to establish a fluid communication path between a position outside the plunger component with the hollow interior, said plunger being generally uniform in outside diameter between said closed end and the third port side of said aperture, said plunger component being inserted into said valve body through said second port closed end first so that said aperture is selectively slidably situated in said first portion and said second portion of said interior cavity; and a first seal located on said plunger component between said closed end and said aperture, wherein said first seal and said aperture are selectively locatable in said first and second portions of said interior cavity, said first seal having a size such that said first seal has an interference fit with said second portion when situated in said second portion, whereby when situated in the second portion, said first seal blocks said fluid communication between said first and second conduits; and said valve body and plunger component having exterior surfaces formed to facilitate engagement thereof by a mechanized actuation mechanism;

whereby said aperture provides for fluid communication between said first and second conduits when said aperture is positioned in said first portion, and whereby said seal blocks said fluid communication between said first and second conduits when said seal is positioned in said second portion.

2. The apparatus of claim 1, wherein said side wall of said plunger component has an exterior side, and said first seal comprises at least one annular ridge formed on said exterior side of said plunger component, said ridge being located adjacent said aperture.

3. The apparatus of claim 1, wherein said first seal comprises at least one ridge formed on said exterior side of said plunger component, and said apparatus further comprises a second seal, said second seal comprising at least one ridge formed on said exterior side of said plunger, and being located between said aperture and said third port, wherein said first and second seals are formed as part of said plunger component and said plunger component is formed wholly of a slightly deformable substance, wherein each of said seals has an interference fit with said second portion of said interior cavity when situated in said second portion.

4. The apparatus of claim 1, wherein said first and second seals are formed as part of said plunger component and said plunger component is formed wholly of a slightly deformable substance, wherein each of said seals has an interference fit with said second portion of said interior cavity when situated in said second portion.

5. The apparatus of claim 1, further comprising an actuation means for selectably positioning said plunger component in a first position in relation to said valve body in which said first seal and said aperture are positioned within said second portion and for selectably positioning said plunger component in a second position in relation to said valve body in which said first seal and said aperture are positioned within said first portion.

6. The apparatus of claim 5, wherein:
said actuation means is capable of moving said plunger component and said valve body in relation to each other so that in said first position, said first seal is moved to a position in said second portion and in said second position, said aperture is positioned in said first portion.

7. An apparatus for controlling fluid communication between a first and a second conduit, comprising:
a valve body having a first port, a second port, and an interior cavity, said cavity having a first portion having a diameter and a second portion having a diameter, wherein both said first and second ports are in fluid communication with said interior cavity and said first port is connected to a first conduit, wherein said diameter of said first portion of the interior cavity is larger than said diameter of said second portion, and said first portion is closer to said first port than said second portion is to said first port;
a plunger component having a closed end, a hollow interior and a third port connected to a second conduit and to said hollow interior, said plunger component having a side wall connecting said third port with said closed end, said side wall having an aperture positioned therein adapted to establish a fluid communication path between a position outside the plunger component with the hollow interior; said plunger component being inserted into said valve body through said second port closed end first so that said aperture is selectively slidably situated in said first portion and said second portion of said interior cavity;
a first seal located on said plunger component between said closed end and said aperture, wherein said first seal and said aperture are selectively locateable in said first and second portions of said interior cavity, said first seal having a size such that said first seal has an interference fit with said second portion when situated in said second portion, whereby when situated in the second portion, said first seal blocks said fluid communication between said first and second conduits;
said valve body and plunger component having exterior surfaces formed to facilitate engagement thereof by a mechanized actuation mechanism;
whereby said aperture provides for fluid communication between said first and second conduits when said aperture is positioned in said first portion, and whereby said seal blocks said fluid communication between said first and second conduits when said seal is positioned in said second portion;
an actuation mechanism comprising:
a first clamp attached to said plunger component;
a second clamp attached to said valve body; and
an actuation element which moves into and out of engagement with one of said clamps and, when in engagement with said clamp, causes said engaged clamp to move in relation to the other of said clamps to thereby cause said plunger component to move in relation to said valve body.

8. The apparatus of claim 7, further comprising biasing means for biasing one of said clamps to a predetermined position in relation to the other of said clamps when said actuation element is not engaged with said one of said clamps.

9. The apparatus of claim 8, wherein said biasing means biases said biased clamp to a position wherein said first seal of said plunger component resides in said second portion of said interior cavity, and said actuating element, when engaged, causes said plunger component and said valve body to move in relation to each other so that said aperture is located in said first portion of said interior cavity so that a flow path is established between said interior cavity and said hollow interior of said plunger component.

10. The apparatus of claim 9, wherein:
said biasing means biases said first and second clamps apart so that said first seal is located in said second portion of said interior cavity; and
said actuation element causes said first clamp and said second clamp to be moved toward one another so that said aperture is moved to said first portion of said interior cavity so that said flow path is established through said interior cavity, through said aperture and through said hollow interior of said plunger component.

11. The apparatus of claim 9, wherein:
said first clamp is rigidly integrated into a housing;
said second clamp comprises a hinged arm;
said biasing means biases said hinged arm to a predetermined position;
said actuation element is rigidly affixed to a structure mounted to said housing such that said actuation element swings into and out of engagement with said arm, and, when swung into engagement with said arm, causes movement of said arm in relation to said first clamp.

12. The apparatus of claim 11, wherein said actuation element is mounted on a cover which is hingedly connected to said housing, and wherein said actuation element engages said hinged arm as said cover is swung closed.

13. The apparatus of claim 12, wherein said hinged arm includes an angled engaging surface to facilitate the movement of said hinged arm upon engagement by said actuation element.

14. An apparatus for controlling fluid communication between a first and a second conduit, comprising:

a valve body having a first port, a second port, and an interior cavity, said cavity having a first portion having a diameter and a second portion having a diameter, wherein both said first and second ports are in fluid communication with said interior cavity and said first port is connected to a first conduit, wherein said diameter of said first portion of the interior cavity is larger than said diameter of said second portion, and said first portion is closer to said first port than said second portion is to said first port;

a plunger component having a closed end, a hollow interior and a third port connected to a second conduit and to said hollow interior, said plunger component having a side wall connecting said third port with said closed end, said side wall having an aperture positioned therein adapted to establish a fluid communication path between a position outside the plunger component with the hollow interior; said plunger component being inserted into said valve body through said second port closed end first so that said aperture is selectively slidably situated in said first portion and said second portion of said interior cavity;

a first seal located on said plunger component between said closed end and said aperture, wherein said first seal and said aperture are selectively locateable in said first and second portions of said interior cavity, said first seal having a size such that said first seal has an interference fit with said second portion when situated in said second port, whereby when situated in the second portion, said firs seal blocks said fluid communication between said first and second conduits; and said valve body and plunger component having exterior surfaces formed to facilitate engagement thereof by a mechanized actuation mechanism;

whereby said aperture provides for fluid communication between said first and second conduits when said aperture is positioned in said first portion, and whereby said seal blocks said fluid communication between said first and second conduits when said seal is positioned in said second portion;

whereby said second portion of said interior cavity includes a protrusion positioned thereon so as to interact with said first seal such that, when said aperture is positioned in said first portion, said firs seal is on a first side of said protrusion and, when said aperture is positioned in said second portion, said first seal is on a second side of said protrusion, said first side of said protrusion being closer than said second side to said first portion of said interior cavity;

wherein sliding said plunger component in said interior cavity so that said first seal is moved between said first and second portions of said interior cavity causes said first seal to come into and out of contact with said first protrusion, said contact providing a tactile and audible indicator of a presence or absence of said fluid communication between the first and second conduits.

15. An apparatus for controlling fluid communication between a first and a second conduit, comprising:

a valve body having a first port, a second port, and an interior cavity, said cavity having a first portion having a diameter and a second portion having a diameter and a first end and a second end, said diameter of said second portion being substantially the same between said first end and said second end, whereby both said first and second ports are in fluid communication with said interior cavity and said first port is connected to a first conduit, wherein the diameter of said first portion of the interior cavity is larger than the diameter of said second portion, and said first portion is closer to said first port than said second portion is to said first port;

a plunger component having a closed end, a hollow interior, and a third port connected to a second conduit and to said hollow interior, said plunger component having a side wall connecting said third port with said closed end, said side wall having an aperture positioned therein adapted to establish a fluid communication path between a position outside the plunger component with the hollow interior, said plunger being generally uniform in outside diameter between said closed end and the third port side of said aperture, said plunger component being inserted into said valve body through said second port closed end first so that said aperture is selectively slidably situated in said first portion and said second portion of said interior cavity; and a first seal located on said plunger component between said closed end and said aperture, wherein said first seal and said aperture are selectively locatable in said first and second portions of said interior cavity, said first seal having a size such that said first seal has an interference fit with said second portion when situated in said second portion, whereby when situated in said second portion, said first seal blocks said fluid communication path between said first and second conduits; and said second portion of said interior cavity includes a first protrusion positioned therein so as to interact with said first seal such that, when said aperture is positioned in said first portion, said first seal is on a first side of said first protrusion and, when said aperture is positioned in said second portion, said first seal is on a second side of said first protrusion, said first side of said first protrusion being closer than said second side of said first protrusion to said first portion of said interior cavity;

whereby said aperture provides for said fluid communication path between said first and second conduits when said aperture is positioned in said first portion, and whereby said seal blocks said fluid communication path between said first and second conduits when said seal is positioned in said second portion.

16. The apparatus of claim 15, wherein said side wall of said plunger component has an exterior side, and said first seal comprises an annular ridge formed on said exterior side of said plunger component, said ridge being located adjacent said aperture.

17. The apparatus of claim 16, wherein said first seal comprises at least one ridge formed on said exterior side of said plunger component, and said apparatus further comprises a second seal and a second protrusion, said second seal comprising at least one ridge formed on said exterior side of said plunger component, said second seal being located between said aperture and said third port and being of sufficient size to have an interference fit with said second portion of said interior cavity when situated in said second portion, said second protrusion being formed in said second portion of said interior cavity, and said first protrusion being closer than said second protrusion to said first portion of said interior cavity, wherein said seals interact with said protrusions to provide a tactile and audible indicator of a presence or absence of said fluid communication path between said first and second conduits.

18. An apparatus for controlling fluid communication between a first and a second conduit, comprising:
   a valve body having a first port, a second port, and an interior cavity, said cavity having a first portion having a diameter and a second portion, having a diameter, whereby both said first and second ports are in fluid communication with said interior cavity and said first port is connected to a first conduit, wherein the diameter of said first portion of the interior cavity is larger than the diameter of said second portion, and said first portion is closer to said first port than said second portion is to said first port;
   a plunger component having a closed end, a hollow interior, and a third port connected to a second conduit and to said hollow interior, said plunger component having a side wall connecting said third port with said closed end, said side wall having an aperture positioned therein adapted to establish a fluid communication path between a position outside the plunger component with the hollow interior, said plunger being generally uniform in outside diameter between said closed end and the third port side of said aperture, said plunger component being inserted into said valve body through said second port closed end first so that said aperture is selectively slidably situated in said first portion and said second portion of said interior cavity; and
   a first seal located on said plunger component between said closed end and said aperture, wherein said first seal and said aperture are selectively locateable in said first and second portions of said interior cavity, said first seal having a size such that said fist seal has an interference fit with said second portion when situated in said second portion, whereby when situated in said second portion, said first seal blocks said fluid communication path between said first and second conduits; and
   said second portion of said interior cavity includes a first protrusion positioned therein so as to interact with said first seal such that, when said aperture is positioned in said first portion, said first seal is on a first side of said first protrusion and, when said aperture is positioned in said second portion, said first seal is on a second side of said first protrusion, said first side of said first protrusion being closer than said second side of said first protrusion to said first portion of said interior cavity;
   whereby said aperture provides for said fluid communication path between said first and second conduits when said aperture is positioned in said first portion, and whereby said seal blocks said fluid communication path between said first and second conduits when said seal is positioned in said second portion;
   an actuation mechanism comprising:
      a first clamp attached to said plunger component;
      a second clamp attached to said valve body; and
      an actuation element which moves into and out of engagement with one of said clamps and, when in engagement with said clamp, causes said engaged clamp to move in relation to the other of said clamps thereby causing said plunger component to move in relation to said valve body, said actuation element including biasing means for biasing one of said clamps to a predetermined position in relation to the other of said clamps when the actuation element is not engaged with said one of said clamps.

19. The apparatus of claim 18, wherein said biasing means biases said biased clamp to a position wherein said first seal of said plunger component resides in said second portion of said interior cavity, and said actuating element, when engaged, causes said plunger component and said valve body to move in relation to each other so that said aperture is located in said first portion of said interior cavity, and said fluid communication path is established between said interior cavity and said hollow interior of said plunger component.

20. The apparatus of claim 19, wherein:
   said first clamp is rigidly integrated into a housing;
   said second clamp comprises a hinged arm;
   said biasing means biases said hinged arm to a predetermined position;
   said actuation element is rigidly affixed to a structure mounted to said housing such that said actuation element swings into and out of engagement with said arm, and, when swung into engagement with said arm, causes movement of said arm in relation to said first clamp.

21. The apparatus of claim 20, wherein said actuation element is mounted on a cover which is hingedly connected to said housing, and wherein said actuation element engages said hinged arm as said cover is swung closed.

22. An apparatus for controlling fluid communication between a first and a second conduit, comprising:
   a valve body having a first port, a second port, and an interior cavity, said cavity having a first portion having a diameter and a second portion having a diameter, wherein both said first and second ports are in fluid communication with said interior cavity and said first port is connected to the first conduit, wherein the diameter of said first portion of the interior cavity is larger than the diameter of said second portion, and said first portion is closer to said first port than said second portion is to said first port;
   a plunger component having a closed end, a hollow interior, and a third port connected to the second conduit and to said hollow interior, said plunger component having a side wall having an exterior side, said side wall connecting said third port with said closed end, said side wall having an aperture positioned therein adapted to establish a fluid communication path between a position outside said plunger component with said hollow interior, said plunger component being inserted in said valve body through said second port so that said closed end aperture is selectively slidably situated in said first portion and said second portion of said interior cavity; and
   a first seal located on said plunger component between said closed end and said aperture, wherein said first seal and said aperture are selectively locatable in said first and second portions of said interior cavity, said first seal having a size such that said first seal has an interference fit with said second portion when situated in said second portion, whereby when situated in said second portion, said first seal blocks said fluid communication path between said first and second conduits; and whereby said aperture provides for said fluid communication path between said first and second conduits when said aperture is positioned in said first portion, and whereby said seal blocks said fluid communication path between said first and second conduits when said seal is positioned in said second portion;

said apparatus further comprising:

an actuation mechanism, comprising:

a first clamp rigidly integrated into a housing and attached to said plunger component;

a second clamp comprising a hinged arm attached to said housing and attached to said valve body;

an actuation element which moves into and out of engagement with one of said clamps and, when in engagement with said clamp, causes said engaged clamp to move in relation to the other of said clamps to thereby cause said plunger component to move in relation to said valve body;

a biasing means for biasing said hinged arm to a predetermined position where said aperture is located in said second portion of said interior cavity;

wherein said actuation element causes said clamps to be moved to a second position in which said aperture is located in said first portion of said interior cavity, said actuation element being mounted on a structure which is mounted so that said structure moves in relation to said housing, and wherein said engagement element engages said hinged arm as said structure is moved towards said housing.

23. The apparatus of claim 22, wherein said second portion of said interior cavity includes a first protrusion positioned so as to interact with said first seal such that, when said first seal is positioned in said second portion, said first seal is on one side of said protrusion and, when said aperture is positioned in said first portion of said interior cavity said first seal is on the other side of said first protrusion, said first side of said first protrusion being closer than said second side of said first protrusion to said first portion of said interior cavity.

24. The apparatus of claim 23, wherein said first seal comprises at least one ridge formed on said exterior side of said plunger component, and said apparatus further comprises a second seal, said second seal comprising at least one ridge formed on said exterior side and being located between said aperture and said third port.

25. The apparatus of claim 24, wherein said first and second seals are formed as part of said plunger component and said plunger component is formed wholly of a slightly deformable substance, wherein said first and second seals have an interference fit with said second portion of said interior cavity when said first and second seals are situated in said second portion.

26. The apparatus of claim 25, wherein said apparatus further comprises a second protrusion formed in said second portion of said interior cavity, said first protrusion being closer than said second protrusion to said first portion of said interior cavity, wherein said first and second seals interact with said first and second protrusions to provide a tactile and audible indicator of a presence or absence of said fluid communication path between said first and second conduits.

* * * * *